US005550300A

United States Patent [19]

Taylor, Jr. et al.

[11] Patent Number: 5,550,300
[45] Date of Patent: *Aug. 27, 1996

[54] GRADIENT CATALYST SYSTEM FOR THE INTEGRATED PRODUCTION OF ISOPROPYL ALCOHOL AND DIISOPROPYL ETHERS

[75] Inventors: Robert J. Taylor, Jr.; Pei-Shing E. Dai, both of Port Arthur; John F. Knifton, Austin, all of Tex.

[73] Assignee: Texaco Chemical Inc., White Plains, N.Y.

[ * ] Notice: The term of this patent shall not extend beyond the expiration date of Pat. No. 5,430,198.

[21] Appl. No.: 338,725

[22] Filed: Dec. 30, 1994

[51] Int. Cl.$^6$ ............................ C07C 41/09; C07C 43/06
[52] U.S. Cl. .................................................. 568/698
[58] Field of Search ............................................. 568/698

[56] References Cited

U.S. PATENT DOCUMENTS

5,430,198  7/1995  Knifton et al. .......................... 568/698

*Primary Examiner*—Gary Geist
*Assistant Examiner*—Dwayne C. Jones
*Attorney, Agent, or Firm*—Kenneth R. Priem; Cynthia L. Hunter; James L. Bailey

[57] ABSTRACT

Disclosed is an integrated process for the generation of a mixture of ethers, such as diisopropyl ether, methyl tertiary butyl ether, and/or isopropyl tertiary butyl ether, from a crude by-product acetone stream composed of acetone, tertiary butyl alcohol and methanol by passing such a stream, in the presence of hydrogen, over a catalyst system characterized by having both a hydrogenation activity gradient along the reactor in one direction and an etherification activity gradient in the opposite direction.

21 Claims, 1 Drawing Sheet

GRADIENT CATALYST SYSTEM FOR THE INTEGRATED PRODUCTION OF ISOPROPYL ALCOHOL AND DIISOPROPYL ETHERS

CROSS-REFERENCE

This application is related to allowed U.S. Ser. Nos. 08/236,807; and 08/287,451 and pending Ser. No. 08/096,873. It is also related to U.S. Pat. Nos. 4,822,921; 4,827,048; 5,099,072; 5,081,318; 5,059,725; 5,157,162; 5,162,592; 5,157,161; 5,183,947; 5,214,217; 5,214,218; 5,220,078; 5,449,838; 5,364,981; 5,430,198; and 5,476,972 all of which are incorporated by reference herein in their entirety.

FIELD OF THE INVENTION

This invention concerns an integrated procedure for the production of high octane blending components for reformulated gasoline such as diisopropyl ether (DIPE), methyl t-butyl ether (MTBE) and isopropyl t-butyl ether (IPTBE), from a low value crude acetone stream containing acetone, methanol and t-butyl alcohol (tBA) which comprises converting the crude acetone stream to a mixture of ethers in the presence of hydrogen over a catalyst system characterized by having both a hydrogenation activity gradient along the reactor in one direction and an etherification activity gradient in the opposite direction.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Of the ethers which can be produced, a great deal of attention has been directed toward the production of methyl tertiary butyl ether (MTBE) for use as a gasoline oxygenate.

U.S. Pat. No. 4,918,244, to Nelson et al., discloses a method of preparing MTBE by continuously feeding t-butyl alcohol and methanol into a solid-acid catalyst bed, in a reactor separator rectification column in the presence of a solid acid catalyst, such as Amberlyst® 15, whereby a product of substantially pure methyl tertiary butyl ether (MTBE) is separated from the reaction mixture.

An article titled "Expanding Refinery Technology leads to New Ether Potential," by William J. Peil, *Fuel Reformulation*, (1992, November/December) p. 34, contains a good review of the potential of ethers other than MTBE for use in meeting the EPA's requirements.

Though MTBE is the most widely produced and discussed ether, other ethers are also being evaluated, such as diisopropyl (DIPE) and ethyl tertiary butyl ether (ETBE). DIPE can be produced from refinery propylene and water with isopropanol as an intermediate in this process. In a variation, isopropyl tertiary butyl ether could be produced by combining isobutylene with isopropanol.

DIPE has similar physical and blending activities to MTBE and TAME and is a perfectly acceptable fuel oxygen source. Wood, A., Chemical Week, Apr. 15, 1992, p. 7.

The higher molecular weight ethers all have blending vapor pressures lower than MTBE, and much lower than ethanol. Their boiling temperatures are also higher than MTBE. Furthermore, higher molecular weight IPTBE has the potential to contribute more octane.

Although there has not been as much discussion regarding the production of IPTBE as there has been for MTBE, it is apparent that with its lower oxygen level and lower vapor pressure, there should be a definite niche for IPTBE in the future of reformulated gasoline.

The β-zeolite catalysts found useful in this integrated process for production of IPA, DIPE, MTBE and IPTBE have been known in the art for some time. One of the earliest disclosures of zeolite beta was in U.S. Pat. No. 3,308,069 (1967) to Wadinger et al.

J. B. Higgins, et al. of Mobil Research and Development published an article in *Zeolites*, 1988, Vol. 8, November, 446–452 titled "The Framework Topology of Zeolite Beta." In the article Higgins et al. disclose what is known about the framework topology of zeolite beta. The information was determined using a combination of model building, distance-least-square refinement and powder pattern simulation.

In an article titled "Cumene Disproportionation over Zeolite β I. Comparison of Catalytic Performances and Reaction Mechanisms of Zeolites," *Applied Catalysis*, 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article, "II. Stability Enhancement with Silica Deposition and Steam Pretreatment", *Ibid*, pp. 209–222, Tsai and Wang disclose their development of two methods to improve the stability of zeolite beta, silica deposition and steam pretreatment.

Zeolites of low acidity can be achieved by a variety of techniques including steaming. In the case of steaming the zeolite can be exposed at elevated temperatures, 500° to 1200° F., preferably (750° to 1000° F.). This treatment is accomplished in 100% steam or an atmosphere of steam and gas which is substantially inert to the zeolite. A similar treatment can be accomplished at a lower temperature using elevated pressure, e.g., from about 350° F. to 700° F. at from about 10 to 200 atmospheres. Specific details of several steaming procedures can be gained from the disclosures of U.S. Pat. Nos. 4,325,994; 4,374,296 and 4,418,235.

Patents in the art which employ zeolite beta relate mainly to dewaxing, and cracking of hydrocarbon feedstock.

An article titled "Beta Zeolite as Catalyst or Catalyst Additive for the Production of Olefins During Cracking or Gas Oil," was written by L Bonetto et al., 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that β-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a β-zeolite catalyst having a Si:Al ratio of at least 30:1 and a hydrogenation component under isomerization conditions.

Another European Application to Mobil, EP 0 094 82, discloses simultaneous catalytic hydrocracking and hydrodewaxing of hydrocarbon oils with β-zeolite.

In European Patent Application 0 095 303, to Mobil, there is a disclosure of dewaxing distillate fuel oils by the use of β-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising a β-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

Large pore β-zeolite has been employed in the synthesis of industrially important para-cumene by toluene isopropylation. See "Toluene Isopropylation over Zeolite β and Metallosilicates of MFI Structure," P. A. Parikh et al., *Applied Catalysis*, A, 1992, 90, p. 1.

In European Patent 323 138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166° C.

In U.S. Pat. No. 5,144,086, to Harandi et al., there is disclosed an integrated multistage process for the production of diisopropyl ether from substantially pure propene wherein in the second stage isopropanol containing about 0–20% water is contacted with an acidic large pore zeolite etherification catalyst which comprises a β-zeolite having a silica to alumina ratio of about 30:1 to 50:1.

In a European Patent, EP 323 268, light olefins are converted to alcohols and/or ethers in the presence of β-zeolite.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

U.S. Pat. No. 4,714,787, to Bell et al., discloses a process for the manufacture of methyl isopropyl ether from methanol and a $C_3$ hydrocarbon fraction that contains 20 to 100 wt. % of propylene, which process comprises preparing a mixture of said hydrocarbon fraction and 0.1 to 10 moles of methanol per mol of propylene contained in said fraction, contacting said mixture with a solid insoluble acid catalyst comprising materials having the structure of zeolite Beta, said contacting being effected under a combination of conditions effective to selectively form said ether.

U.S. Pat. No. 5,225,609 to Bell discloses a process for the production of alkyl tertiary alkyl ether employing a zeolite catalyst, particularly zeolite beta which is pretreated either by steaming or hydrothermal treatment using liquid water at elevated temperatures. This process is claimed to be particularly effective in reducing the formation of dimer by-product in the zeolite Beta catalyzed process for the formation of methyl tertiary butyl ether (MTBE) with high selectivity.

The use of faujasite zeolites in alkyl ether formation is also known in the art. The following references discuss the use of faujasite zeolites in various applications.

Japanese Patent 82-07432 teaches the use of zeolites, particularly mordenites and faujasites, to make dialkyl ethers containing primary or secondary alkyl groups by the liquid phase dehydration of alcohols.

In allowed U.S. Pat. No. 5,214,217, to Texaco Chemical Company, there is disclosed a method for preparing methyl tertiary butyl ether by reacting butanol and methanol in the presence of a catalyst comprising a super-acid alumina or a faujasite-type zeolite.

In U.S. Pat. No. 5,081,318, a Y-type zeolite modified with fluorosulfonic acid is disclosed.

In U.S. Pat. No. 3,955,939, to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140° –170° C., in the presence of a catalyst comprising a super-acid alumina or a faujasite-type zeolite.

It is also known in the art to produce IPA and DIPE by the hydration of propylene and subsequent dehydration of IPA to DIPE.

In U.S. Pat. No. 5,208,387, also to Harandi et al., there is disclosed a process for the acid catalyzed production of DIPE from propene and water feed stream that eliminates the propene recycle stream to the olefin hydration reactor and achieves high propene conversion. This process is carried out in two stages wherein the first stage comprises a zeolite catalyzed hydration and etherification of propene employing a minimum of water feed and the second stage converts unconverted propene from the first stage reactor by hydration and etherification to DIPE.

In an article titled "Race to License New MTBE and TAME Routes Heats Up", Rotman D., *Chemical Week*, Jan. 6, 1993, p. 48, there is a review of new technology at several different companies which centers around skeletal isomerization, particularly of $C_4$ and $C_5$ olefins. The interest in this technology is fueled by the promise of dramatically increased and relatively inexpensive isobutylene and isoamylene that could boost MTBE and TAME production, often constrained by the amounts of available isobutylene in refinery or steam cracker streams. DIPE production from propylene is also discussed.

Mobil Corp. has disclosed new etherification technology that can produce fuel oxygenates based only on olefinic refinery streams and water. This process has the potential to allow refiners to produce oxygenates without having to rely on an external supply of alcohols. The technology is developed around diisopropyl ether (DIPE) based on propylene. Wood, A., supra, p. 7.

In related U.S. Pat. No. 5,449,838 there is disclosed a two-step process for generation of isopropyl t-butyl ether from crude acetone.

In related U.S. Pat. No. 5,430,198 there is disclosed a two-step process for the generation of diisopropyl ether from a crude by-product acetone stream which comprises hydrogenating said crude acetone over a bulk metal, nickel-rich catalyst to give an isopropanol effluent and subjecting said isopropanol-rich intermediate to dehydration conditions in the presence of a strong acid zeolite catalyst. This process requires interstage separation of the hydrogen prior to the dehydration step. In related U.S. Pat. No. 5,476,972 discloses a one-step process for the generation of DIPE from a crude acetone by-product stream using a single bifunctional catalyst which contains both hydrogenation and etherification activity.

It does not appear that there is any disclosure or suggestion in the art of converting acetone to ethers in an integrated process having a catalyst configuration wherein a hydrogenation activity gradient exists along the reactor bed in one direction and an etherification activity gradient exists along the bed in the other direction.

The by-product stream containing low-value crude acetone typically contains about 20% to 80% acetone. The by-product acetone stream may also contain greater than 5% of both methanol (MeOH) and t-butanol (tBA) and typically in the range of 10% to 40% methanol and t-butanol. It would greatly enhance the economics of any process to produce MTBE or other oxygenates if acetone, along with some methanol and t-butanol, from a by-product stream could be converted to oxygenates such as DIPE, IPTBE and MTBE.

SUMMARY OF THE INVENTION

In accordance with the foregoing, the method of the instant invention is an improvement over the method described in allowed copending U.S. Ser. No. 08/236,807, incorporated herein by reference in its entirety, and comprises generation of diisopropyl ether, isopropyl tertiary butyl ether, and methyl tertiary butyl ether from a crude by-product acetone stream in an integrated process by reacting said crude acetone over a series of catalyst zones at a temperature of 50° –200° C., a pressure of 100 to 1000 psig, and a space velocity 0.1–10 LHSV wherein the hydrogenation function of the catalyst decreases and the etherification function increases along successive zones of the catalyst bed in a fixed bed or catalytic distillation reactor, and wherein the metal loading ranges from 40–25% to 20–10% to 5–0% metals, and zeolite concentration of the supports range from 0–5% to 60–40% to 90–70% along the length of the bed. The metal in the catalysts consist essentially of one or more metals from Group IB and VIII from the Periodic Table. The catalyst support is made of oxides selected from Group III or IV oxides such as alumina, silica-alumina, zirconia, zirconia-alumina and, optionally, contains an acidic zeolite selected from the group consisting of β-zeolite, dealuminized Y-zeolite, large-pore silicoaluminophosphate molecular sieves such as SAPO-5, and medium-pore silicoaluminophosphate molecular sieves such as SAPO-11. The zeolite is, optionally, modified with one or more metals from Groups IB and VIII of the Periodic Table. When the by-product feed stream contains methanol and t-butanol, the process also provides methyl tertiary butyl ether (MTBE) and isopropyl tertiary butyl ether (IPTBE). The instant process permits the production of desirable ether products without producing large quantities of undesirable gas products.

DETAILED DESCRIPTION OF THE INVENTION

In a process to make propylene oxide a large number of by-products are typically generated with the desired product. The by-products may include formic acid, acetic acid, their ester derivatives, t-butanol and acetone. The acetone may constitute about 20% to 80% of certain crude by-product streams. These crude acetone streams may be further mixed with methanol and t-butanol in significant amounts. The acetone stream may contain greater than 5% of methanol and t-butanol and typically in the range of 10% to 40%.

Figure 1:
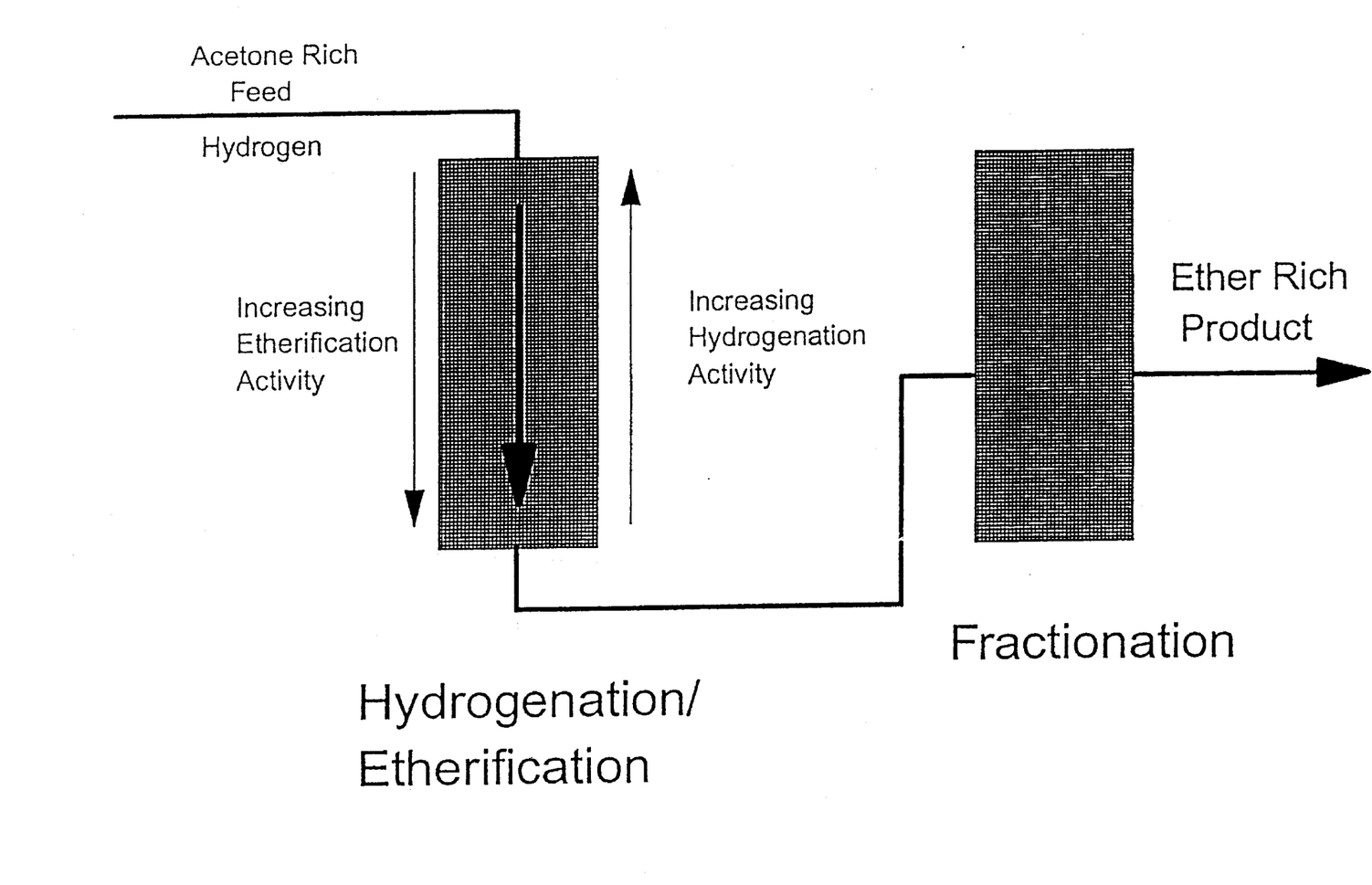
The drawing represents a process for producing ethers from crude acetone using a gradient catalyst bed.

U.S. Pat. No. 5,430,198 discloses a two-step process for generation of DIPE from crude by-product stream which requires interstage separation of hydrogen. Removal of hydrogen can cause propylene to oligomerize in the etherification reactor. In a commercial process this can greatly increase costs for purification of the DIPE product and regeneration of the catalyst. Also relevant is allowed copending Ser. No. 08/236,807 which describes a process using a separate hydrogenation and etherification catalyst in an integrated process, wherein the effluent from the hydrogenation reactor is fed directly into the etherification reactor without interstage separation of hydrogen.

U.S. Pat. No. 5,476,972 describes a process for preparing DIPE from acetone in a one-step process which uses a single catalyst to carry out both the hydrogenation and dehydration functions in a single reactor.

The instant invention describes an integrated process like that described in U.S. Pat. No. 5,476,972 except the catalyst configuration is such that a hydrogenation activity gradient exists along the reactor bed in one direction and an etherification activity gradient exists along the bed in the other direction. The advantage of this catalyst configuration is the minimization of unwanted reactions which produce C6/C9 liquid products and C3 gas products.

The crude acetone stream is reacted over catalyst in a series of zones, wherein the initial zone contains a high hydrogenation function and low etherification function and successive zones contain decreasing hydrogenation function and increasing etherification function and the metal loadings range, for example, from 40–25% to 20–10% to 5–0% metals and zeolite concentrations in the support from 0–5% to 60–40% to 90–70% along the length of the bed.

The desired reactions involved in this integrated process can be represented by:

In the top section of a down-flow fixed bed reactor, the crude acetone stream is passed over a catalyst which has high hydrogenation activity and low etherification activity. The total metals loading of the catalyst is the range of 25 to 40 wt % based on the total catalyst. The support material is selected from the group of low acidity oxides consisting of alumina, zirconia-alumina, titania-alumina and magnesia-alumina and, optionally, combined with a zeolite selected from the group of beta zeolite, dealuminate zeolite Y, large-pore silicoaluminophosphate molecular sieves such as SAPO-5, and medium-pore silicoaluminophosphate molecular sieves such as SAPO-11. The concentration of zeolite in the support in the first zone is in the range of 0–5%. The preferred support for the catalyst used in the first zone is a low acidity oxide, such as alumina, with no zeolite present. A preferred catalyst is characterized by having a metals composition, calculated in mol % of the total metals, of from about 60–85% nickel, and 1–30% copper with the preferred proportions being about 65–88% nickel and 12–35% copper.

In the middle section of the reactor, the effluent from the top section is passed over a catalyst which has medium hydrogenation activity and medium etherification activity. The total metals loading of the catalyst is the range of 10 to 20 wt %. The support material is selected from the group of low acidity oxides consisting of alumina, zirconia-alumina, titania-alumina and magnesia-alumina and combined with a zeolite from the group of beta zeolite, dealuminate zeolite Y or large-pore silicoaluminophosphate (SAPO) or medium pore SAPO molecular sieves. The concentration of zeolite in the support is in the range of 40–60%. The preferred support for the catalyst used in the middle zone is a low acidity oxide, such as alumina, with 50–60% zeolite present. A preferred catalyst is characterized by having metals composition, calculated in mol % of the total metals, of from about 60–85% nickel, and 1–30% copper with the preferred proportions being about 65–88% nickel, and 12–35% copper.

In the bottom section of the reactor, the effluent from the middle section is passed over a catalyst which has low hydrogenation activity and high etherification activity. The total metals loading of the catalyst is the range of 0 to 5 wt %. The support material is selected from the group of low acidity oxides consisting of alumina, zirconia-alumina, titania-alumina and magnesia-alumina and combined with a zeolite from the group of beta zeolite, dealuminate zeolite Y or large-pore silicoaluminophosphate (SAPO) or medium pore SAPO molecular sieves. The concentration of zeolite in the support is in the range of 70–90%. The preferred support for the catalyst used in the bottom zone is a low acidity oxide, such as alumina, with 75–85% zeolite present. A preferred catalyst is characterized by having metals composition, calculated in mol % of the total metals, of from about 60–85% nickel, and 1–30% copper with the preferred proportions being about 65–88% nickel, and 12–35% copper.

The catalyst in the top zone is designed to give a high conversion of acetone to IPA (reaction 1) without significant condensation of acetone to undesirable C6 and C9 products or the dehydration of IPA to C3 gas and water. As the acetone/IPA stream passes further down the reactor, the remaining acetone is reduced and the alcohols are etherified in the catalyst zones with increasing quantities of acidic functionality, such as, for example, beta zeolite or dealuminated zeolite Y. Acetone conversions of 98+ percent are achieved with an ether rich effluent containing a high concentration of IPA and ethers, such as, for example, DIPE, MTBE, IPTBE. Fractionation of this ether rich effluent can yield high octane fuel ethers for use as gasoline blending components.

The zeolite incorporated in the catalyst support can optionally be exchanged with one or more ions from Group IB or VIII metals, including, but not limited to nickel and copper prior to being formed with a binder of Group III and/or Group IV Oxides. In this instant embodiment, the metals can be impregnated on a support comprised of a zeolite in combination with an oexide of Group III or IV of the Periodic Table. This is demonstrated in Examples 1 to 4.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

$$[XNa(1.0\pm0.1-X)TEA]AlO_2 YSiO_2 \cdot WH_2O$$

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, Supra, p. 446, the first clues to the crystal structure of zeolite beta were evidenced from chemical and physical property measurements. Ion-exchange isotherms of Na-β at 25° C. indicated that cations as large as tetraethylammonium (TEA$^+$) exchanged completely into the pore system. This behavior suggests that beta contains at least 12-membered rings opening into channels, because TEA$^+$is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm$^3$ ruled out undimensional pore systems such as those in ZSM-12, ZSM-22, ZSM-23 and ZSM-48. Structural similarities among beta, mordenite and ZSM-12 were suspected because all three may be synthesized in Na$^+$–TEA$^+$ systems from highly siliceous batch compositions. Further, zeolite beta is easily synthesized in the SiO$_2$/Al$_2$O$_3$ range of 30–50. This lies between TEA$^+$mordenite (typically 10–30) and ZSM-12 (typically, >60), suggesting the beta framework contains large fractions of both 4- and 5-membered rings.

In the Tsai and Wang reference, Supra, part II, p. 209, stability enhancement is discussed. Two methods, silica deposition and steam pretreatment, have been developed to substantially improve zeolite beta stability.

Ibid, p. 215, it is stated that zeolite beta has two types of three dimensional pore openings, the linear and the tortuous channel. The former has pore openings of 7.5Å×5.7Åand the latter has pore openings of 6.5Å×5.6Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

$$[X/n]M(1\pm0.1-X)H]AlO_2 YSiO_2 \cdot WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

| d Values of Reflection in zeolite beta |
| --- |
| 11.40 ± 0.2 |
| 7.40 ± 0.2 |
| 6.70 ± 0.2 |
| 4.25 ± 0.1 |
| 3.97 ± 0.1 |
| 3.00 ± 0.1 |
| 2.20 ± 0.1 |

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m²/g.

Suitable β-zeolites for the practice of this invention include Valfor® C806β, Valfor CP815β and Valfor® C861. Valfor® is the registered trademark of the PQ Corporation. Valfor® C806β zeolite is zeolite beta powder in template cation form. It is a high silica shape selective zeolite which contains the organic template used in the crystallization step, having been isolated after filtration and washing of the synthesis product. C806β has a $SiO_2/Al_2O_3$ molar ratio of 23–26; the crystal size is 0.1–0.7 um; the surface area after calcination is about 700–750 m²/g; the cyclohexane adsorption capacity after calcination is 19–24g/100g; $Na_2O$ content is about 0.01–1.0% by weight anhydrous; and, the organic content is about 11–13% by weight, on a water-free basis.

Valfor® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a $SiO_2/Al_2O_3$ molar ratio of about 23–26; the crystal size, surface area, cyclohexane adsorption capacity and $Na_2O$ are all within the same ranges as given for C806β.

Valfor® C861β is an extrudate made of 80% C815β powder and 20% alumina powder.

Y-zeolites are also useful and are from the group of faujasite zeolites. The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$Na_{56}[(AlO_2)_{56}(SiO_2)_{136}]x.250\ H_2O$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum-atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

As demonstrated in related, U.S. Pat. No. 5,430,198 these Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents or by treatment with fluorine or a fluorine-containing compound such as silicon tetrafluoride or ammonium fluorosilicate, or hydrothermal treatment and/or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of catalysts having a silica-to-alumina ratio of 5 to 25 and particularly 5 to 10.

Examples of suitable commercially available dealuminized Y-zeolites include UOP's LZY-82 and LZY-72, PQ corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

| ZEOLITE TYPE | UNIT CELL SIZE, A | $SiO_2/Al_2O_3$ MOLAR |
| --- | --- | --- |
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

Said catalysts may be formed in the presence of a binder, such as Group III or Group IV oxide. Group IV oxides used in conjunction with said β-zeolite include oxides of aluminum, silicon, and titanium, zirconium, as well as combinations thereof. Alumina is preferred. Said binders may comprise 10% to 90% of the formed catalyst.

Particularly effective in the subject integrated production of DIPE, MTBE and IPTBE are the β-zeolites, optionally bound to an oxide, modified with multiple metals.

The metals useful for modifying the zeolite in the instant invention comprise those from Groups IB and VIII of the Periodic Table. Preferred metals are those found in Groups IB and VIII of the Periodic Table and include copper, nickel, palladium and platinum. Especially good results were observed using combinations of nickel and copper on a β-zeolite in combination with alumina.

Said catalyst supports are preferably impregnated with said specified metals as their salts, particularly their metal nitrate or chloride salts, in an aqueous, alcoholic, or ketonic media over a period of 1–24 hours, then the solids are dried at elevated temperature, e.g. 120° C., for a period of time and calcined at 300°–800° C. for a further period, e.g. 315° C. for 2 hours, followed by 540° C. for another 2 hours, then reduced in a stream of hydrogen at $\geq 200°$ C.

The amount of the various metals deposited on the catalyst can vary. The amount of each individual metal, i.e., copper, nickel, palladium and platinum can vary from 0.01 to 40%. Where copper and nickel are deposited on zeolite/alumina extrudates the preferred total weight percent is from 0.1% to 40%.

Said catalysts may be in the form of powders, pellets, granules, spheres, shapes and extrudates. The examples described herein demonstrate the usage of granules.

The process of the instant invention is carried out in a series of catalyst zones containing decreasing hydrogenation function and increasing etherification function along the length of the catalyst bed. The hydrogenation reaction of crude acetone stream is performed in a liquid phase downflow or upflow fixed bed reactor or a catalytic distillation reactor. The catalyst could be packed (loaded) into one, or more than one, zone with a quench zone in between the catalyst zones. The heat evolved from the catalyst zone with high hydrogenation functionality could be effectively removed by the quench stream, which allows better control of the reactor temperature. The reactor system can be fixed bed or catalytic distillation column or more than one reactors in series.

Dehydration to the oxygenates can generally be conducted at temperatures from 20° to 250° C.; the preferred range is 80° to 200° C. Good results are observed throughout this temperature range, however, it can be noted that the best conversion figures for MTBE, DIPE and IPTBE cogeneration are observed when the temperature is 50°–200° C. The total operating pressure may be from 0 to 2000 psig, or higher. The preferred pressure range is 100 to 1000 psi.

Typically, DIPE is generated continuously in up to ca. 35 wt % concentration or greater in the crude liquid product at total liquid hourly space velocities (LHSV) of 0.1–10/ hour and relatively mild conditions, where:

$$LHSV = \frac{\text{Volume Of Total Liquid Feed Run Into The Reactor Per Hour}}{\text{Volume of Catalyst In Reactor}}$$

It is anticipated that MTBE and IPTBE can be generated in up to 15 and 20 wt % concentration or greater, respectively.

Conversions of pure acetone or crude acetone are estimated in the following examples using the equation:

$$\frac{(\text{Mole \% of Acetone in Feed} - \text{Mole \% of Acetone in Product})}{\text{Mole \% of Acetone in Feed}} \times 100$$

The examples which follow illustrate the integrated process for the synthesis of DIPE, IPTBE and MTBE, from a 97+% pure acetone feed, and, optionally, a crude acetone stream containing acetone, tBA, and MeOH, using a catalyst similar to that in copending Ser. No. 08/188,007, incorporated herein by reference in its entirety, with the improvement comprising utilizing a catalyst configuration where zones of catalyst having varying percentages of metal and zeolite give a catalyst bed with decreasing hydrogenation functions and increasing etherification functions along its length.

Catalyst screening runs were performed in a microreactor test unit which has two reactors in series separated by a quench zone. The reactors were operated in a downflow configuration. The top reactor was loaded with 4 cc of catalyst. The second reactor had two catalyst beds of 4 cc catalyst each separated by a 4 cc bed of inert material. The total charge of catalyst was 12 cc in the unit. Internal thermocouples were positioned at the bottom of each catalyst bed and at the inlet to the first reactor. The liquid feed was charged to the unit using a high pressure pump and the hydrogen was metered through a mass flow controller. For the purpose of simplifying the analysis of liquid products by GC, pure acetone (technical grade, 97%) was used as a feedstock to demonstrate the chemistry involved in the instant invention.

The catalysts were activated by heating slowly from room temperature to 500° F. over a 6 hour period under flowing nitrogen at 70 psig. The unit pressure was then raised to 500 psig with hydrogen and the catalyst bed was held at 500° F. for 10 hours under flowing hydrogen. The catalyst bed was cooled down to below 200° F. The acetone feed was charged to the unit at 1 LHSV based on total catalyst volume. The hydrogen flow rate was controlled to give a hydrogen to acetone mole ratio of 5:1 and a total pressure of 500 psig. The acetone feed was mixed with hydrogen and preheated to 200° F. It was then fed into the first reactor which contained the catalyst with the highest hydrogenation activity and the lowest etherification activity. The first reactor was operated adiabatically. The feed left the first reactor and entered the second reactor. The top bed in the second reactor contained the catalyst which had an intermediate hydrogenation and etherification activity. The bottom bed in the second reactor contained the catalyst which had the lowest hydrogenation activity and the highest etherification activity. The liquid product was collected periodically from a chilled receiver at 0° F. and 300 psig. The product was analyzed by gas chromatography to determine the composition of hydrocarbon and oxygenates, and by Karl-Fischer titration for the water content.

Examples 1 through 4 demonstrate preparation of the catalysts. Examples 5 through 8 demonstrate the screening of the catalysts. Each example included a series of runs, the data for which is recorded in Tables I and II.

EXAMPLE 1

Sample 052-93-6896-031 was prepared by impregnating 46g of an alumina support with 37 ml of a solution prepared by 46.94g of nickel nitrate and 4.95 g of copper nitrate dissolved in distilled water. The catalyst was dried at 250° F. for 16 hours. The dried catalyst was then impregnated with 30 ml of a solution prepared by dissolving 46.93 g of nickel nitrate and 4.95 g of copper nitrate in distilled water. The catalyst was then dried at 250° F. for 16 hours and calcined at 600° F. for 4 hours and 900° F. for 8 hours.

EXAMPLE 2

Samples 052-92-6888-045 and 052-93-6919-019 were prepared by impregnated 50 g of a support containing 50% zeolite beta and 50% alumina with 40 ml of a solution prepared by 51 g of nickel nitrate and 5.4 g of copper nitrate dissolved in distilled water. The catalyst was then dried at 250° F. for 16 hours and calcined at 600° F. for 4 hours and 900° F. for 8 hours.

EXAMPLE 3

Sample 052-92-6919-119 was prepared by impregnating 50 g of a support containing 80% zeolite beta and 20% alumina with 44 ml of a solution prepared by 25.5g of nickel nitrate and 2.7 g of copper nitrate dissolved in distilled water. The catalyst was then dried at 250° F. for 16 hours and calcined at 600° F. for 4 hours and 900° F. for 8 hours.

EXAMPLE 4

Sample 052-93-6919-020 was prepared by impregnating 50 g of a support containing 10% zeolite beta and 90% alumina with 38 ml of a solution prepared by 51 g of nickel nitrate and 5.4 g of copper nitrate dissolved in distilled water. The catalyst was dried at 250° F. for 16 hours. The dried catalyst was then impregnated with 34 ml of a solution prepared by dissolving 51 g of nickel nitrate and 5.4 g of copper nitrate in distilled water. The catalyst was then dried at 250° F. for 16 hours and calcined at 600° F. for 4 hours and 900° F. for 8 hours.

EXAMPLE 5

In Run 097-93-6024, catalyst 052-93-6896-031 (32% NiCu on alumina) was loaded in the top bed, 052-93-6888-045 (16% NiCu on 50% beta/50% alumina) was loaded in the middle bed and 052-93-2138-000 (0% metals on 80% beta/20% alumina) was loaded in the bottom bed. In this configuration, the metal loading goes from 32% to 16% to 0% metals and 0% to 50% to 80% zeolite content along the length of the bed. (NOTE: The zeolite contents quoted here are for percent based on support and not based on metal/support catalysts). It clearly can be seen in this example that at acetone conversion of 98+% IPA and DIPE can be made in high concentrations with very little side reactions to produce $C_3$ gas or $C_6/C_9$ condensation products.

EXAMPLE 6

In Run 097-93-6033, catalyst 052-93-6919-020 (32% NiCu on 10% beta/90% alumina) was loaded in the top bed, 052-93-6919-019 (16% NiCu on 50% beta/50% alumina) was loaded in the middle bed and 052-93-6919-119 (8% metals on 80% beta/20% alumina) was loaded in the bottom bed. In this configuration, the metal loading goes from 32% to 16% to 8% metals and 10% to 50% to 80% zeolite content along the length of the bed. (NOTE: The zeolite contents quoted here are for percent based on support and not based on metal/support catalysts). It clearly can be seen in this example that at acetone conversions of 98+%, IPA and DIPE can be made in high concentrations with very little side reactions to $C_3$ gas or $C_6/C_9$ condensation products.

EXAMPLE 7

This example illustrates the co-generation of DIPE, MTBE and IPTBE from a mixed alcohol feedstock. The synthesis was conducted in a tubular reactor (½ in. i.d., 12 in. long) constructed of 316 stainless steel, operated upflow, and mounted in a furnace, controllable to +or–1C. The reactor was loaded with 50 cc of CP861 beta zeolite (80% beta, 20% alumina binder, 1/16 in. extrudates). A glass wool screen was placed at the top and bottom of the reactor to ensure the catalyst remains in the middle of the reactor. The catalyst bed was contacted with a mixed alcohol feedstock containing 33 wt % isopropyl alcohol and 67 wt % tertiary butyl alcohol while the reactor was held at a series of temperatures (40–140 C). The pressure was maintained at 700 psig and the flow rate at 0.25 LHSV.

At 60° C., the TBA conversion is 25% with DIPE and IPTBE concentrations of 0.1 wt % and 14.7 wt %, respectively At 120° C., the TBA conversion is 90% with a DIPE and IPTBE concentration of 5.7 wt % and 1.1 wt %, respectively At 140° C., the TBA conversion is 98% with a DIPE and IPTBE concentration of 16.9 wt % and 0.2 wt, respectively

EXAMPLE 8

In a separate reactor run, beta zeolite catalyst was contacted with another feedstock containing 11% methanol, 29% IPA and 58% TBA at 700 psig and 0.25 LHSV. At 60° C., the TBA conversion is 44% and the MTBE and IPTBE effluent concentrations are 17.3 and 7.3 wt %, respectively.

It is clearly advantageous to have a process which utilizes the activity gradient catalyst system disclosed here, as seen in Table A. This table compares a process using the activity gradient catalyst system to those using a single catalyst, one-step process and a dual catalyst, two-step process. The activity gradient process clearly maximizes the DIPE production and minimizes the C3 gas formation.

TABLE A

| Process | Mid Bed Temp, °F. | IPA, wt % | DIPE, wt %* | Gas, wt %* |
|---|---|---|---|---|
| One-Step, A | 264 | 65 | 20 | 15 |
| Two-Step, B | 295 | 53 | 37 | 10 |
| Act. Grad., C | 302 | 57 | 42 | 1 |

*based on dehydrated product
A - Zone 1,2,3: 32% Ni/Cu on 50% Beta
B - Zone 1: 32% Ni/Cu on alumina
Zone 2,3: 60% Beta
C - Zone 1: 32% Ni/Cu on 10% Beta
Zone 2: 16% Ni/Cu on 50% Beta
Zone 3: 8% Ni/Cu on 80% Beta

TABLE I (Example 5)
Run No. 097-93-6024

| Catalyst: | Top Bed | 052-93-6896-031 | (Example 1) | 32% NiCu on Alumina Support |
|---|---|---|---|---|
| | Middle Bed | 052-92-6888-045 | (Example 2) | 16% NiCu on 50% Beta Support |
| | Bottom Bed | 052-93-2138-000 | | 80% Beta Catalyst |

| | | | | | Liquid | PRODUCT COMPOSITION | | | | | |
|---|---|---|---|---|---|---|---|---|---|---|---|
| Cut No. | TOS Hr. | Top Bed | Mid. Bed | Bot. Bed | Recov. wt. % | C3 wt % | Acetone wt % | IPA wt % | DIPE wt % | $C_6C_9$ wt % | Water wt % |
| 100 | 6 | 213° F. | 267° F. | 272° F. | 99 | 0.2 | 0.0 | 81.6 | 13.6 | 0.0 | 3.5 |

TABLE I-continued (Example 5)
Run No. 097-93-6024

| Catalyst: | Top Bed | 052-93-6896-031 | (Example 1) | 32% NiCu on Alumina Support |
| --- | --- | --- | --- | --- |
| | Middle Bed | 052-92-6888-045 | (Example 2) | 16% NiCu on 50% Beta Support |
| | Bottom Bed | 052-93-2138-000 | | 80% Beta Catalyst |

| Cut No. | TOS Hr. | Top Bed | Mid. Bed | Bot. Bed | Liquid Recov. wt. % | C3 wt % | Acetone wt % | IPA wt % | DIPE wt % | $C_6C_9$ wt % | Water wt % |
| --- | --- | --- | --- | --- | --- | --- | --- | --- | --- | --- | --- |
| 200 | 9 | 211 | 274 | 262 | 100 | 0.3 | 0.0 | 74.9 | 20.0 | 0.0 | 4.9 |
| 300 | 12 | 214 | 280 | 287 | 98 | 0.5 | 0.5 | 64.5 | 26.3 | 0.0 | 6.6 |
| 400 | 14 | 212 | 290 | 283 | 100 | 0.7 | 0.0 | 58.4 | 32.7 | 0.0 | 8.1 |
| 500 | 22 | 215 | 276 | 264 | 100 | 0.5 | 0.0 | 71.3 | 22.8 | 0.0 | 5.4 |
| 600 | 27 | 215 | 302 | 290 | 100 | 0.7 | 0.5 | 51.1 | 37.4 | 0.0 | 10.3 |
| 700 | 32 | 220 | 318 | 294 | 94 | 1.1 | 1.0 | 42.5 | 37.5 | 0.0 | 11.9 |

TABLE II (Example 6)
Run No. 097-93-6033

| Catalyst: | Top Bed | 052-93-6819-020 | (Example 4) | 32% NiCu on 10% Beta Support |
| --- | --- | --- | --- | --- |
| | Middle Bed | 052-92-6919-019 | (Example 2) | 16% NiCu on 50% Beta Support |
| | Bottom Bed | 052-93-6919-119 | | 8% NiCu on 80% Beta Support |

| Cut No. | TOS Hr. | Top Bed | Mid. Bed | Bot. Bed | Liquid Recov. wt. % | C3 wt % | Acetone wt % | IPA wt % | DIPE wt % | $C_6C_9$ wt % | Water wt % |
| --- | --- | --- | --- | --- | --- | --- | --- | --- | --- | --- | --- |
| 200 | 15 | 222° F. | 265° F. | 265° F. | 100 | 0.0 | 0.0 | 86.5 | 9.9 | 0.3 | 3.3 |
| 300 | 19 | 221 | 287 | 277 | 99 | 0.7 | 0.0 | 64.9 | 26.0 | 0.3 | 7.7 |
| 400 | 21 | 221 | 285 | 270 | 100 | 0.5 | 0.0 | 71.6 | 21.9 | 0.0 | 6.0 |
| 500 | 31 | 225 | 295 | 282 | 96 | 0.6 | 0.0 | 65.3 | 24.4 | 0.0 | 6.0 |

What is claimed is:

1. An integrated process for the generation of DIPE from a crude byproduct acetone stream by reacting the crude acetone with hydrogen over a catalyst system consisting of a series of catalyst zones in a reactor characterized by a hydrogenation activity gradient along the reactor in one direction and an etherification activity gradient in the opposite direction, wherein the catalysts in these zones display hydrogenation activity resulting from the presence of one or more metals from Group IB and Group VIII and etherification activity resulting from a support containing a strong acid zeolite from the group consisting of Beta zeolite, dealuminated Y zeolite, medium-pore and large-pore silicoaluminophosphates, optionally, mixed with a binder selected from Groups III and IV of the Periodic Table, wherein the concentration of metals and zeolite are varied in the catalysts along the length of the catalyst bed resulting in an activity gradient for hydrogenation which decreases along the bed and an activity gradient for etherification which increases along the length of the bed.

2. The integrated process of claim 1 wherein the crude byproduct acetone stream contains about 20% to 100% acetone and the process also provides diisopropyl ether (DIPE).

3. The integrated process of claim 2 wherein the crude byproduct acetone stream also contains about 10% to 70% methanol and t-butanol and the process also provides methyl tertiary butyl ether (MTBE) and isopropyl tertiary butyl ether (IPTBE).

4. The integrated process of claim 2 wherein the catalyst gradient comprises metal loading ranges from 40–25% to 20–10% to 5–0% metals and a support with a zeolite concentration in the range 0–5% to 60–40% to 90–70% along the length of the bed.

5. The process of claim 4 wherein the metal composition of the catalysts, based on mol % of total metals, are 60–85 wt % nickel and 1–30 wt % Cu.

6. The process of claim 2 wherein the β-zeolite has a silica:alumina molar ratio of at least 10:1.

7. The process of claim 2 wherein the β-zeolite has a silica:alumina molar ratio in the range of 10:1 to 50:1.

8. The process of claim 1 wherein the β-zeolite has a surface area, after calcination, of at least 100 m²/g.

9. The process of claim 1 wherein the β-zeolite is characterized by the following X-ray diffraction, pattern:

| |
| --- |
| 11.40 ± 0.2 |
| 7.40 ± 0.2 |
| 6.70 ± 0.2 |
| 4.25 ± 0.1 |
| 3.97 ± 0.1 |
| 3.00 ± 0.1 |
| 2.20 ± 0.1 |

10. The process of claim 1 wherein the β-zeolite catalyst is formed in the presence of a binder selected from a Group III oxide or a Group IV oxide.

11. The process of claim 10 wherein the Group III oxide binder is alumina.

12. The process of claim 11 wherein the alumina comprises 10% to 90% of the formed catalyst.

13. The process of claim 1 wherein the β-zeolite is modified with one or more metals from Groups IB and VIII of the Periodic Table.

14. The process of claim 13 wherein the β-zeolite is modified with one or more metals selected from the group consisting of copper, nickel, palladium and platinum.

15. The process of claim 13 wherein the concentrations of metals deposited on said zeolite may vary from 0.01% to 10.0% for each metal.

16. The process of claim 1 wherein the zeolite catalyst is a dealuminated Y-zeolite selected from the group consisting of
   a) a Y-zeolite exchanged with ammonium followed by calcination;
   b) a Y-zeolite treated with ethylenediaminetetraacetic acid
   c) a Y-zeolite treated with a fluorine-containing compound from the group consisting of silicon tetrafluoride and ammonium fluorosilicate; or
   d) a Y-zeolite treated with steam alone or followed by acid treatment.

17. The process of claim 16 wherein the dealuminized Y-zeolite has a silica-to-alumina molar ratio of greater than 3.

18. The process of claim 17 wherein the Y-zeolite is dealuminated and has a silica-to-alumina molar ratio in the range 7 to 50 and a unit cell size in the range 24.26 Å to 24.56 Å.

19. The process of claim 1 wherein the zeolite catalyst is a medium-pore silicoaluminophosphate molecular sieve including SAPO-11, SAPO-41, MgAPSO-31.

20. The process of claim 1 wherein the zeolite catalyst is a large-pore silicoaluminophosphate molecular sieve including SAPO-5, SAPO-37, MgAPSO-36 and MgAPSO-46.

21. The process of claim 1 wherein the generation of DIPE, MTBE, IPTBE from crude acetone stream is conducted at a temperature of 50°–200° C., a pressure of 100–1000 psig, and a liquid hourly space velocity of 0.1–10.

* * * * *